United States Patent
Kishi et al.

(10) Patent No.: US 10,571,382 B2
(45) Date of Patent: Feb. 25, 2020

(54) DYNAMIC MOISTURE PERMEABILITY EVALUATION APPARATUS

(71) Applicant: NITTO DENKO CORPORATION, Ibaraki-shi, Osaka (JP)

(72) Inventors: Atsushi Kishi, Ibaraki (JP); Yasutaka Ishihara, Ibaraki (JP); Satoru Mamiya, Ibaraki (JP)

(73) Assignee: NITTO DENKO CORPORATION, Ibaraki-shi (JP)

( * ) Notice: Subject to any disclaimer, the term of this patent is extended or adjusted under 35 U.S.C. 154(b) by 223 days.

(21) Appl. No.: 15/703,549

(22) Filed: Sep. 13, 2017

(65) Prior Publication Data

US 2018/0088019 A1 Mar. 29, 2018

(30) Foreign Application Priority Data

Sep. 23, 2016 (JP) .................................. 2016-186117

(51) Int. Cl.
*G01N 15/08* (2006.01)

(52) U.S. Cl.
CPC .......... *G01N 15/082* (2013.01); *G01N 15/08* (2013.01); *G01N 15/0806* (2013.01); *G01N 15/0826* (2013.01)

(58) Field of Classification Search
USPC .......................................................... 73/38
See application file for complete search history.

(56) References Cited

U.S. PATENT DOCUMENTS

| 3,286,509 A * | 11/1966 | Gluckman ............. G01N 15/08 73/38 |
| 2004/0123646 A1* | 7/2004 | Echigo ............... G01N 15/0826 73/38 |
| 2007/0227233 A1* | 10/2007 | Norenberg ......... G01N 15/0826 73/38 |

(Continued)

FOREIGN PATENT DOCUMENTS

| JP | 2015-114386 A | 6/2015 |
| WO | 2011/132391 A1 | 10/2011 |

OTHER PUBLICATIONS

Extended European Search Report dated Feb. 2, 2018, issued in counterpart European Application No. 17191817.0. (10 pages).

*Primary Examiner* — Paul M. West
*Assistant Examiner* — Mark A Shabman
(74) *Attorney, Agent, or Firm* — Westerman, Hattori, Daniels & Adrian, LLP

(57) ABSTRACT

A water vapor concentration in a test gas in a first space of a measurement space in which a sample is disposed is adjusted, and a water vapor concentration m a earlier gas in a second space separated from the first space by the sample is measured by a measurement unit. When the water vapor concentration in the test gas is changed, a shift B in charge of the water vapor concentration in the carrier gas from the change of the water vapor concentration in the test gas is calculated. The calculated shift B in the change of the water vapor concentration in the carrier gas corresponds to ease of moisture accumulation in the sample. Thus, it is possible to analyze not only the amount of moisture permeating the sample but also the ease of moisture accumulation, so that characteristics of the sample can be widely analyzed.

15 Claims, 2 Drawing Sheets

(56) References Cited

U.S. PATENT DOCUMENTS

| | | | |
|---|---|---|---|
| 2008/0060418 A1* | 3/2008 | DeRoos | G01N 15/0826 73/38 |
| 2009/0158817 A1* | 6/2009 | Welt | G01N 15/0826 73/38 |
| 2010/0017148 A1 | 1/2010 | Bos et al. | |
| 2010/0154513 A1* | 6/2010 | Lin | B01D 46/42 73/38 |
| 2010/0294025 A1* | 11/2010 | Omori | G01N 15/08 73/38 |
| 2014/0013824 A1 | 1/2014 | Welt | |
| 2014/0223999 A1* | 8/2014 | Graehlert | G01N 15/0826 73/38 |

* cited by examiner

DYNAMIC MOISTURE PERMEABILITY EVALUATION APPARATUS

TECHNICAL FIELD

The present invention relates to a dynamic moisture permeability evaluation apparatus, a method for evaluating dynamic moisture permeability, and a dynamic moisture permeability evaluation program for evaluating dynamic moisture permeability of a sample in a measurement chamber separated into a first space and a second space by the sample.

BACKGROUND

Conventionally, as shown in paragraph [0110] and the like of Japanese Unexamined Patent Application Publication No. 2015-114386, a moisture permeation amount measuring apparatus (e.g., a water vapor permeability measuring apparatus "PERMATRAN" manufactured by MOCON, Inc., etc.) for instantly measuring moisture permeability of a sample with high accuracy has been used. Using this type of apparatus enables measurement of the amount of moisture permeating various samples, such as a single film and a multilayer film having a multilayer laminated structure.

For example, a polarizing plate is a multilayer film in which a base film, a polarizer, an adhesive layer, and the like are laminated. A polarizing plate potentially has low durability in a wet heat test, and the moisture permeability and moisture amount in each layer thereof are very important. Each layer constituting a polarizing plate has its own moisture permeability, and when each layer is individually measured using a moisture permeation amount measuring apparatus, the moisture permeability of each layer can be calculated. It has been thought that durability of a polarizing plate in which these layers are laminated can be estimated in design based on the moisture permeability and moisture amount of each layer.

However, in a process of studying durability of a polarizing plate for wet heat, the inventors of the present invention have found that moisture permeability of each layer constituting the polarizing plate is different between in a single layer state and in a laminated state. It is considered that this is caused by receiving interaction such as internal pressure due to difference in linear expansion of each of the laminated layers and existence of internal stress caused through a stretching process.

In a conventional moisture permeation amount measuring apparatus, it is impossible to analyze moisture permeability of each layer in a multilayer film, such as a polarizing plate, in a state where each layer is laminated. Therefore, this does not enable analysis of characteristics (moisture permeability and moisture amount) of each layer of a multilayer film used while each layer is laminated in a state where the multilayer film is actually used. In addition, the conventional moisture permeation amount measuring apparatus can only measure moisture permeability of not only the multilayer film but also a sample, and thus it is difficult to widely analyze moisture permeability of a sample when a water vapor concentration is changed (hereinafter referred to as also "dynamic moisture permeability").

Further, such a problem is a new problem that arises not only in the case of analyzing dynamic moisture permeability of a sample when water vapor is used as a specimen, but also in the case of analyzing dynamic gas permeability of a sample when another specimen gas such as oxygen, carbon dioxide, or the like is used.

The present invention has been made in light of the above-mentioned circumstances, and it is an object of the present invention to provide a dynamic moisture permeability evaluation apparatus, a method for evaluating dynamic moisture permeability, and a dynamic moisture permeability evaluation program, capable of widely analyzing characteristics of a sample. Another object of the present invention is to provide a dynamic moisture permeability evaluation apparatus, a method for evaluating dynamic moisture permeability, and a dynamic permeability evaluation program, capable of evaluating characteristics in any layer in a sample.

SUMMARY OF THE INVENTION (1) A dynamic moisture permeability evaluation apparatus according to the present invention includes a measurement chamber, a test gas flow system a test gas adjustment system, a control unit, a carder gas flow system, a measurement unit, and an analysis unit. In the measurement chamber, a sample is disposed, and the sample separates the measurement chamber into a first space and a second space. The test gas flow system allows a test gas to continuously flow into the first space. The test gas adjustment system adjusts a water vapor concentration in the test gas in the first space. The control unit causes the test gas adjustment system to change the water vapor concentration in the test gas. The carrier gas flow system allows a carrier gas to continuously flow into the second space. The measurement unit measures a water vapor concentration in the carder gas. The analysis unit analyzes a shift in change of the water vapor concentration in the carrier gas measured by the measurement unit from change of the water vapor concentration in the test gas, when the water vapor concentration in the test gas is changed by the control unit.

According to the configuration described above, it is possible to analyze characteristics of a sample based on the shift in change of the water vapor concentration in the carrier gas from change of the water vapor concentration in the test gas, the shift being calculated by changing the water vapor concentration in the test gas. The calculated shift in the change of the water vapor concentration in the carrier gas corresponds to ease of moisture accumulation in the sample. Thus, it is possible to analyze not only the amount of moisture permeating the sample but also the ease of moisture accumulation, so that characteristics of the sample can be widely analyzed.

(2) The control unit may cause the test gas adjustment system to periodically change the water vapor concentration in the test gas. In this case, the analysis unit may perform waveform analysis based on a waveform indicating a periodic change of the water vapor concentration in the test gas, and a waveform indicating aperiodic change of the water vapor concentration in the carrier gas measured by the measurement unit, with respect to the change of the water vapor concentration in the test gas.

According to the configuration described above, the waveform analysis when the water vapor concentration in the test gas is periodically changed enables the characteristics of the sample to be widely analyzed. Specifically, a height of the waveform corresponds to moisture permeability, and a shift in the waveforms is caused by ease of moisture accumulation, so that the characteristics of the sample can be analyzed. In addition, changing a frequency of the periodic change of the water vapor concentration in the test gas stepwise or continuously leads to evaluation of detailed characteristics of the sample based on frequency dependence of the water vapor concentration in the test gas.

(3) The control unit ma change a frequency of periodic change of the water vapor concentration in the test gas stepwise or continuously. In this case, the analysis unit may perform waveform analysis at each frequency.

According to the configuration described above, when the waveform analysis is performed at each frequency, an internal structure of the sample can be evaluated based on frequency dependence of the water vapor concentration in the test gas.

(4) The test gas adjustment system may adjust the water vapor concentration and temperature in the test gas. In this case, the control unit may cause the test gas adjustment system to change the water vapor concentration and temperature in the test gas. In addition, the analysis unit may calculate a shift in change of the water vapor concentration in the carrier gas measured by the measurement unit from change of the water vapor concentration in the test gas at each temperature, when temperature of the test gas is changed by the control unit and the water vapor concentration in the test gas at each temperature is changed by the control unit.

According to the configuration described above, when a shift in change of the water vapor concentration in the carrier gas from change of the water vapor concentration in the test gas at each temperature is calculated by changing temperature of the test gas, characteristics of the sample can be analyzed based on the shift.

The control unit may cause the gas adjustment system to periodically change temperature of the test gas. In this case, the analyzing unit may perform waveform analysis based on a waveform indicating a periodic change of the temperature of the test gas and a waveform indicating a periodic charge of the water vapor concentration in the carrier gas measured by the measurement unit, with respect to the change in the temperature. Changing a frequency of the periodic change in the temperature stepwise or continuously leads to evaluation of detailed characteristics of the sample based on frequency dependency of the temperature of the test gas.

(5) A dynamic gas permeability evaluation apparatus according to the present invention includes a measurement chamber, a test gas flow system, a test gas adjustment system, a control unit, a earlier gas flow system, a measurement unit, and an analysis unit. In the measurement chamber, a sample is disposed, and the sample separates the measurement chamber into a first space and a second space. The test gas flow system allows a test gas to continuously flow into the first space. The test gas adjustment system adjusts a concentration of a specimen in the test gas in the first space. The control unit causes the test gas adjustment system to change a concentration of the specimen in the test gas. The carrier gas flow system allows a carrier gas to continuously flow into the second space. The measurement unit measures a concentration of the specimen in the carrier gas. The analysis unit analyzes a shift in change of the concentration of the specimen in the carrier gas measured by the measurement unit from change of the concentration of the specimen in the test gas, when the concentration of the specimen in the test gas is changed by the control unit.

According to the configuration described above it is possible to analyze characteristics of the sample based on the shift in change of the concentration of the specimen in the earlier gas from change of the concentration of the specimen in the test gas, the shift being calculated by changing the concentration of the specimen in the test gas. The calculated shift in the change of the water vapor concentration in the carrier gas corresponds to ease of moisture accumulation in the sample. Thus, it is possible to analyze not only the amount of the specimen permeating the sample but also the ease of specimen accumulation, so that characteristics of the sample can be widely analyzed.

(6) A method for evaluating dynamic moisture permeability according to the present invention includes the steps of disposing a sample; allowing a test gas to flow; allowing a carrier gas to flow; performing control; and performing analysis. In the step of disposing a sample, a sample is disposed in a measurement chamber and the sample separates the measurement chamber into a first space and a second space. In the step of allowing a test gas to flow, a test gas is allowed to continuously flow into the first space. In the step of allowing a carrier gas to flow, a carrier gas is allowed to continuously flow into the second space. In the step of performing control, a water vapor concentration in the test gas is changed. In the step of performing analysis, there is performed analysis of a shift in change of the water vapor concentration in the carrier gas from change of the water vapor concentration in the test gas when the water vapor concentration in the test gas is changed in the step of performing control.

(7) A method for evaluating dynamic gas permeability according to the present invention includes the steps of disposing a sample; allowing a test gas to flow allowing a carrier gas to flow; performing control; and performing analysis. In the step of disposing a sample, a sample is disposed in a measurement chamber and the sample separates the measurement chamber into a first space and a second space. In the step of allowing a test to flow a test gas is allowed to continuously flow into the first space. In the step of allowing a carrier gas to flow, a carrier gas is allowed to continuously flow into the second space. In the step of performing control, a concentration of a specimen in the test gas is changed. In the step performing analysis, there is performed analysis of a shift in change of the concentration of the specimen in the carrier gas from change of the concentration of the specimen in the test gas when the concentration of the specimen in the test gas is changed in the step of performing control.

(8) A non-transitory computer readable recording medium storing a dynamic moisture permeability evaluation program according to the present invention is configured to evaluate dynamic moisture permeability of a sample in a measurement chamber separated into a first space and a second space by the sample, the program causing a computer to execute the steps of allowing a test gas to flow; allowing a carrier gas to flow; performing control; and performing analysis. In the step of allowing a test gas to flow, a test gas is allowed to continuously flow into the first space. In the step of allowing a carrier gas to flow, a carrier gas is allowed to continuously flow into the second space. In the step of performing control, a water vapor concentration in the test gas is changed. In the step of performing analysis, there is performed analysis of a shift in change of the water vapor concentration in the carrier gas from change of the water vapor concentration in the test gas when the water vapor concentration in the test gas is changed in the step of performing control.

(9) A non-transitory computer readable recording medium storing a dynamic gas permeability evaluation program according to the present invention is configured to evaluate dynamic gas permeability of a sample m a measurement chamber separated into a first space and a second space by the sample, the program causing a computer to execute the steps of: allowing a test gas to flow; allowing a carrier gas to flow; performing control; and performing analysis. In the step of allowing a test gas to flow, a test gas is allowed to continuously flow into the first space. In the step of allowing a carrier gas to flow, a carrier gas is allowed to continuously flow into the second space. In the step of performing control, a concentration of a specimen in the test gas is changed. In the step performing analysis, there is performed analysis of a shift in change of the concentration of the specimen in the carrier gas from change of the concentration of the specimen in the test gas when the concentration of the specimen in the test gas is changed in the step of performing control.

According to the present invention, it is possible to analyze not only the amount of moisture permeating the sample but also the ease of moisture accumulation, so that characteristics of the sample can be widely analyzed. In addition, according to the present invention, characteristics in any layer in a sample can be evaluated by using waveform analysis.

DETAILED DESCRIPTION OF THE PREFERRED EMBODIMENTS

1. Structure of Measurement Chamber

Figure 1:
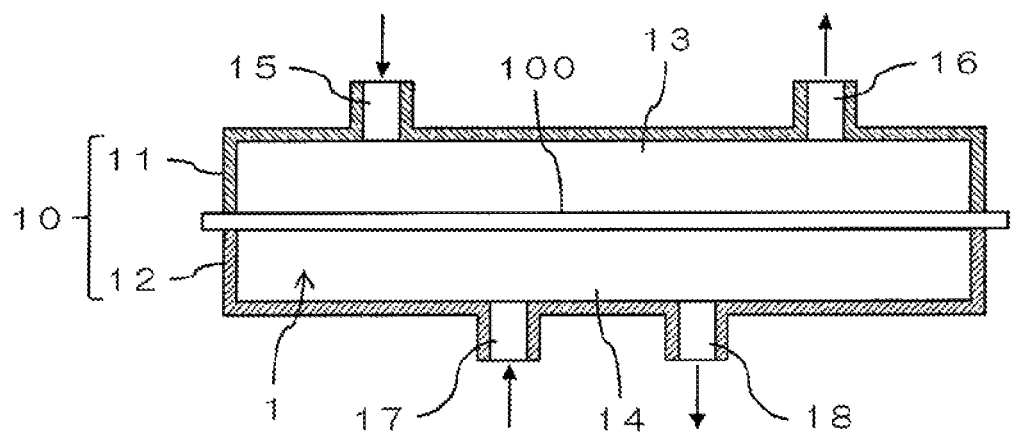
FIG. 1 is a schematic sectional view illustrating a structure of a measurement chamber in a dynamic moisture permeability evaluation apparatus according to an embodiment of the present invention.

FIG. 1 is a schematic sectional view illustrating a structure of a measurement chamber 1 in a dynamic moisture permeability evaluation apparatus according to an embodiment of the present invention. The measurement chamber 1 is formed inside a casing 10. The casing 10 includes a first casing 11 and a second casing 12, and the first casing 11 and the second casing 12 are stacked on each other to form the measurement chamber 1 inside the casing 10.

A sample 100 to be measured is inserted between the first casing 11 and the second casing 12 so that a portion other than a peripheral portion of the sample 100 is disposed in the measurement chamber 1. In this state, the measurement chamber 1 is separated into the first space 13 and the second space 14 by the sample 100. In the present embodiment, the case where the sample 100 is a film member (film-shaped sample) will be described, but the sample 100 is not limited to the film member.

The first casing 11 is provided with an inflow port 15 and an outflow port 16. Gas flows into the first space 13 defined by the first casing 11 and the sample 100 from the inflow port 15. The gas flowing into the first space 13 is a test gas adjusted to a set water vapor concentration (humidity). This allows the first space 13 to be filled with the test gas, and the test gas exceeding the capacity of the first space 13 overflows from the outflow port 16. The inflow port 15 and the outflow port 16 constitute a test has flow system for allowing the test gas to continuously flow into the first space 13.

The second casing 12 is provided with an inflow port 17 and an outflow port 18. Gas flows into the second space 14 defined by the second casing 12 and the sample 100 from the inflow port 17. The gas flowing into the second space 14 is a carrier gas composed of a dry gas (e.g., nitrogen gas) from which moisture is removed. This all the second space 14 to be filled with the carrier gas, and the second space 14 is kept in a state where a water vapor concentration is lower than that of the first space 13. As a result, moisture (water vapor) contained in the test gas in the first space 13 permeates the sample 100 and flows into the second space 14 to allow the carrier gas in the second space 14 to contain moisture. The carrier gas containing moisture in the second space 14 overflows through the outflow port 18, and a water vapor concentration detection unit (not illustrated) detects a water vapor concentration of the carrier gas. The inflow port 17 and the outflow port 18 constitute a carrier gas flow system for allowing the carrier gas to continuously flow into the second space 14.

2. Composition of Sample

Figure 2:
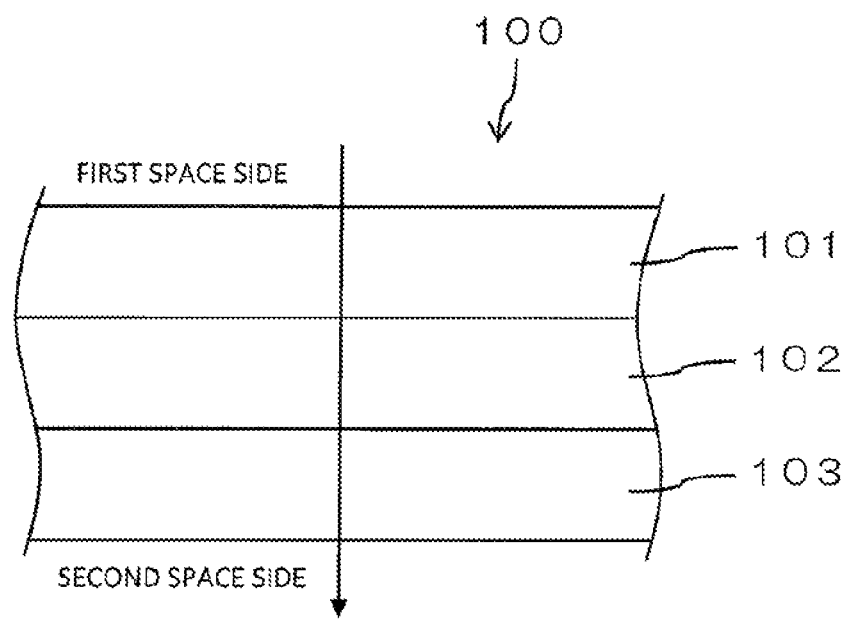
FIG. 2 is a schematic sectional view illustrating an example of the composition of a sample.

FIG. 2 is a schematic sectional view illustrating an example of the composition of a sample 100. In the present embodiment, the sample 100 to be measured is a multilayer film in which a plurality of layers 101, 102, and 103 is laminated, for example. More specifically, the sample 100 is a polarizing plate in which a base film 101, a polarizer 102, an adhesive layer 103, and the like are laminated, for example. Each of the layers 101, 102, and 103 has a thickness of from a few micrometers to a few tens micrometers, for example.

The sample 100 is disposed in the measurement chamber 1 such that the base film 101 is on a first space 13 side and the adhesive layer 103 is on a second space 14 side, for example. In this case, moisture contained in a test gas in the first space 13 permeates the base film 101, the polarizer 102, and the adhesive layer 103 in this order as indicated by an arrow in FIG. 2, and is mixed into a carrier gas in the second space 14.

Each of the layers 101, 102, and 103 has its own moisture permeability, and moisture contained in the test gas in the first space 13 accumulates little by little in the layers and interfaces between the corresponding layers in a process of permeating the layers 101, 102, and 103. Accordingly, a ratio of moisture (moisture content) contained in each of the layers 101, 102, and 103 has a different value before and after moisture contained in the test gas in the first space 13 permeates each of the layers 101, 102, and 103.

The moisture permeability of each of the layers 101, 102, and 103 constituting the sample 100 is different between a single layer state and a laminated state of each of the layers 101, 102, and 103. It is considered that this is caused by receiving interaction such as internal pressure due to difference in linear expansion of each of the laminated layers 101, 102, and 103, and existence of internal stress caused through a stretching process. In the present embodiment, a main object is to measure the amount of moisture permeating the sample 100 in a state where the layers 101, 102, and 103 are laminated, and to analyze characteristics of each of the layers 101, 102, and 103 based on the measurement result.

3. Configuration of Dynamic Moisture Permeability Evaluation Apparatus

Figure 3:
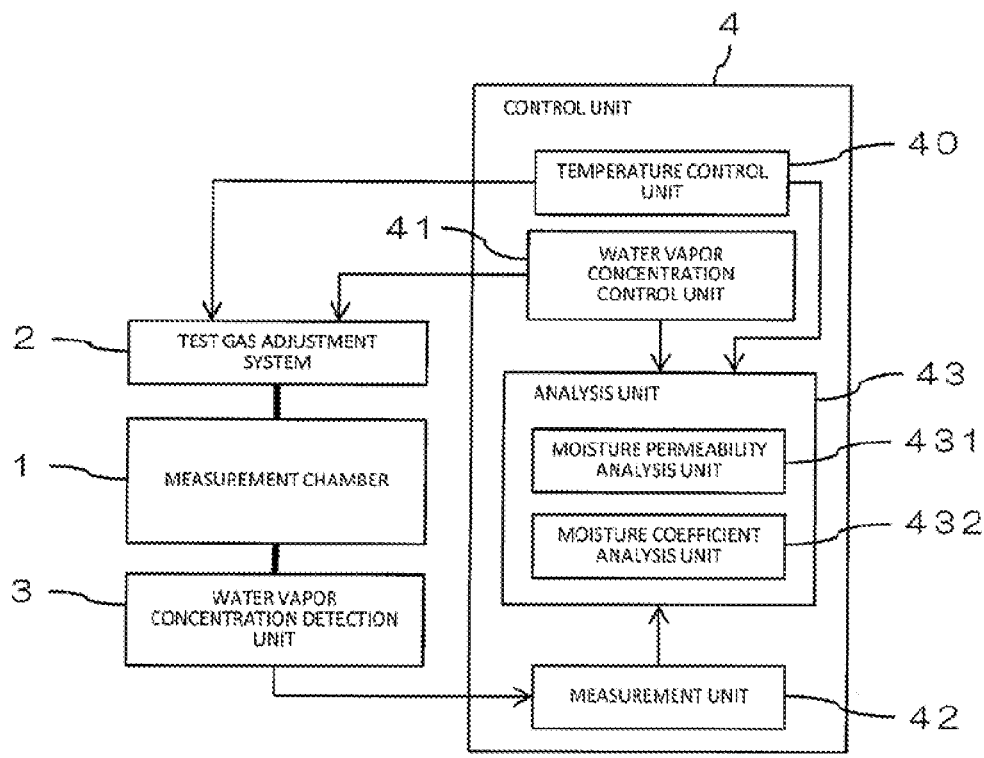
FIG. 3 is a block diagram illustrating an example of a configuration of a dynamic moisture permeability evaluation apparatus.

FIG. 3 is a block diagram illustrating an example of a configuration of a dynamic moisture permeability evaluation apparatus. In addition to the configuration described above, the dynamic moisture permeability evaluation apparatus of the present embodiment also includes a test gas adjustment system 2, a water vapor concentration detection unit 3, a control unit 4, and the like, for example.

The test gas adjustment system 2 adjusts a water vapor concentration and temperature of a test gas flowing into the measurement chamber 1 (in the first space 13) from the inflow port 15. Controlling the test gas adjustment system 2 enables each of the water vapor concentration and the temperature of the test gas in the first space 13 to be adjusted to any value. That is, the water vapor concentration and the temperature of the test gas in the first space 13 can be kept constant or varied.

The water vapor concentration detection unit 3 detects a water vapor concentration in a carrier gas flowing out from the measurement chamber 1 (in the second space 14) through the outflow port 18. The carrier gas flowing into the second space 14 from the inflow port 17 is a dry gas, so that it is possible to calculate the amount of moisture permeating into the second space 14 from the first space 13 based on the water vapor concentration detected by the water vapor concentration detection unit 3.

The control unit 4 is composed of control device such as a computer. The control unit 4 includes a central processing unit (CPU), for example, and serves as a temperature control unit 40, a water vapor concentration control unit 41, a measurement unit 42, an analysis unit 43, and the like, when the CPU executes a program. The analysis unit 43 includes a moisture permeability analysis unit 431 and a moisture coefficient analysis unit 432.

The temperature control unit 40 causes the test gas adjustment system 2 to change temperature of the test gas in the measurement chamber 1 (in the first space 13). The water vapor concentration control unit 41 causes the test gas adjustment system 2 to change a water vapor concentration in the test gas in the measurement chamber 1 (in the first space 13). The measurement unit 42 measures a water vapor concentration in the carrier gas based on a detection signal from the water vapor concentration detection unit 3.

The analysis unit 43 analyzes characteristics of the sample 100 based on a control mode of the test gas adjustment system 2 in each of the temperature control unit 40 and the water vapor concentration control unit 41, and a measurement result of the water vapor concentration in the carrier gas in the measurement unit 42. In the present embodiment, the moisture permeability of the sample 100 can be analyzed by the moisture permeability analysis unit 431, and the moisture coefficient can be analyzed by the moisture coefficient analysis unit 432. Here, the moisture permeability is a value representing ease of moisture permeation, and corresponds to a permeability rate. In addition, the moisture coefficient means a value representing ease of moisture accumulation.

4. Method for Analyzing Sample

Figure 4:
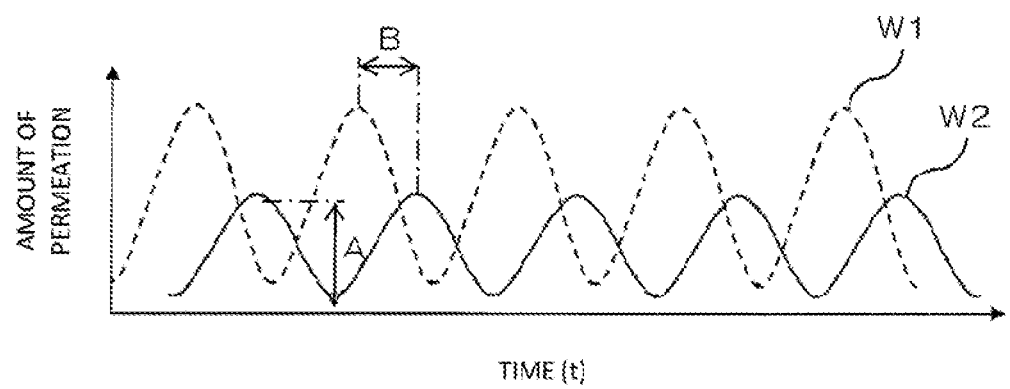
FIG. 4 is a graph for describing a method for analyzing a sample.

FIG. 4 is a graph for describing a method for analyzing the sample 100. In the present embodiment, the water vapor concentration control unit 41 causes the test gas adjustment system 2 to periodically change a water vapor concentration in the test gas in the measurement chamber 1 (in the first space 13), and then the characteristics of the sample 100 are analyzed based on a measurement result of the water vapor concentration (permeation amount) in the carrier gas in the measurement unit 42 at that time. In FIG. 4, where the horizontal axis represents time and the vertical axis represents the amount of permeation (water vapor concentration), the amount of permeation (output) measured by the measurement unit 42 is indicated by the solid line, and periodic change (input) of the water vapor concentration in the test gas in the first space 13 is indicated by the broken line in association with the amount of permeation.

In the example of FIG. 4, the water vapor concentration control unit 41 controls the test gas adjustment system 2 such that the water vapor concentration in the test gas in the first space 13 varies as a sine curve. However, variations of the water vapor concentration in the test gas in the first space 13 may be a periodic change, and thus the water vapor concentration can be varied in other various modes such as a cosine curve. In this case, a waveform W1 indicating the periodic change of the water vapor concentration in the test gas in the first space 13, being input, is shifted from a waveform W2 indicating the periodic change of the water vapor concentration in the carrier gas measured by the measurement unit 42, being output. The present invention is configured to widely analyze the characteristics of the sample 100 by analyzing (waveform analysis) a shift of output from that of input, such as described above.

Specifically, a height A of the waveform W2 of the water vapor concentration (amount of permeation) in the carrier gas, which corresponds to the waveform W1 of the change of the water vapor concentration in the test gas, is a value corresponding to moisture permeability of the sample 100, and a shift B (shift in time) of the waveform W2 from the waveform W1 is a value corresponding to ease of moisture accumulation (moisture coefficient) in the sample 100. Thus, when these values A and B each are considered as a complex number, the characteristics of the sample 100 can be analyzed by using a complex number $(A+B\times i)$ where moisture permeability corresponding to A is a real part (Re), and a moisture coefficient corresponding to B is an imaginary part (Im).

In addition, when a frequency of the periodic change of the water vapor concentration in the test gas in the first space 13, being input, is changed stepwise or continuously, characteristics of any layer and interlayer also can be evaluated from frequency dependence of the water vapor concentration in the test gas. That is, even when the sample 100 in which the plurality of layers 101, 102 and 103 is laminated as illustrated in FIG. 2 is measured in a state where the layers are laminated, changing the frequency of the waveform W1 of input enables analysis of characteristics (moisture permeability and moisture coefficient) of any one of the layers and interfaces corresponding to the frequency. Specifically, at each frequency, there is performed analysis (waveform analysis) of a shift between the waveform W1 indicating the periodic change of the water vapor concentration in the test gas in the first space 13, and the waveform W2 indicating the periodic change of the water vapor concentration (amount of permeation) in the carrier gas measured by the measurement unit 42, with respect to the change of the water vapor concentration in the test gas. At this time, it is possible to evaluate an internal state of the sample from a trajectory acquired by plotting characteristics at each frequency on a Nyquist diagram or a Bode diagram.

The analysis method as described above can be performed at each temperature by changing temperature in the measurement chamber 1 (in the first space 13). That is, when the temperature control unit 40 changes temperature of the test gas in the measurement chamber 1, and the water vapor concentration control unit 41 changes the water vapor concentration in the test gas in the measurement chamber 1 at each temperature, a shift in change of the water vapor concentration (amount of permeation) in the carrier gas measured by the measurement unit 42 from change of the water vapor concentration at each temperature may be calculated. For example, waveform analysis as described above may be performed by changing the water vapor concentration in the test gas in the measurement chamber 1 at different respective temperatures such as 40° C., 50° C., 60° C. and 70° C.

5. Function Effect

In the present embodiment, when the water vapor concentration in the test gas in the first space 13 is varied (control step), and a shift B in change of the water vapor concentration in the earlier gas measured by the measurement unit 42 from the change of the water vapor concentration is calculated by the analysis unit 43 (analysis step), the characteristics of the sample 100 can be analyzed based on the shift B. The calculated shift B in the change of the water vapor concentration in the carrier gas corresponds to ease of moisture accumulation (moisture coefficient) in the sample 100 as described above. Thus, it is possible to analyze not only the amount of moisture permeating the sample 100 but also the ease of moisture accumulation, so that characteristics of the sample 100 can be widely analyzed.

In the present embodiment, the characteristics of the sample 100 can be widely analyzed by waveform analysis of comparing the waveform W1 indicating the periodic change of the water vapor concentration in the test gas in the first space 13, with the waveform W2 indicating the periodic change of the water vapor concentration in the carrier gas measured by the measurement unit 42, with respect to the change of the water vapor concentration in the test gas. Specifically, as described above, moisture permeability can be analyzed based on the height A of the waveform W2, and ease of moisture accumulation (moisture coefficient) can be analyzed based on the shift B between the waveforms W1 and W2. The waveform W2 indicating the periodic change of the water vapor concentration in the carrier gas shows the characteristics of the sample 100 at the position corresponding to a frequency of the waveform W1 indicating the periodic change of the water vapor concentration in the test gas, so that characteristics in any layer in the sample 100 can be evaluated by arbitrarily setting the frequency as described above.

6. Modification

In the above embodiment, the configuration in which the water vapor concentration control unit 41 periodically changes the water vapor concentration in the test gas in the measurement chamber 1 by controlling the test gas adjustment system 2 is described. However, the configuration may be such that the water vapor concentration in the test gas in the measurement chamber 1 may be changed regularly or irregularly in a mode other than the periodic change.

The sample 100 is not limited to a multilayer film, and may be a single film. In addition, the dynamic moisture permeability evaluation apparatus according to the present invention can also measure the sample 100 other than a film.

While the configuration of the dynamic moisture permeability evaluation apparatus is described in the above embodiment, it is also possible to provide a program (dynamic permeability evaluation program) for causing a computer to serve as the control unit 4 of the dynamic moisture permeability evaluation apparatus. In this case, the program may be provided while being stored in a storage medium, or the program itself may be provided.

The present invention is also applicable to a dynamic gas permeability evaluation apparatus, a method for evaluating dynamic gas permeability, and a dynamic gas permeability evaluation program, firm evaluating dynamic gas permeability not only for water vapor but also for various specimens such as oxygen and carbon dioxide.

The invention claimed is:

1. A dynamic moisture permeability evaluation apparatus comprising:
    a measurement chamber that is capable of housing a sample, the sample separating the measurement chamber into a first space and a second space;
    a test gas flow system configured to allow a test gas to continuously flow into the first space;
    a test gas adjustment system configured to adjust a water vapor concentration of the test gas in the first space;
    a control unit configured to cause the test gas adjustment system to change the water vapor concentration of the test gas represented by a waveform W1;
    a carrier gas flow system configured to allow a carrier gas to continuously flow into the second space;
    a measurement unit configured to measure a change of water vapor concentration in the carrier gas represented by a waveform W2; and
    an analysis unit that is capable of analyzing a shift in time of the waveform W2 from the waveform W1.

2. The dynamic moisture permeability evaluation apparatus according to claim 1, wherein
    the waveform W1 has periodical change, and
    the analysis unit is capable of performing waveform analysis based on the waveforms W1 and W2.

3. The dynamic moisture permeability evaluation apparatus according to claim 2, wherein
    the control unit is configured to change a frequency of the periodical change of the water vapor concentration in the test gas stepwise or continuously, and
    the analysis unit is capable of performing waveform analysis at each frequency.

4. The dynamic moisture permeability evaluation apparatus according to claim 1, wherein
    the test gas adjustment system is configured to adjust the water vapor concentration and temperature in the test gas,
    the control unit is configured to cause the test gas adjustment system to change the water vapor concentration and temperature of the test gas, and
    the analysis unit is capable of calculating a shift in time of the waveform W2 from the waveform W1 at each temperature.

5. A dynamic gas permeability evaluation apparatus comprising:
    a measurement chamber that is capable of housing a sample, the sample separating the measurement chamber into a first space and a second space;
    a test gas flow system configured to allow a test gas to continuously flow into the first space;
    a test gas adjustment system configured to adjust a concentration of a specimen gas in the test gas in the first space;
    a control unit configured to cause the test gas adjustment system to change the concentration of the specimen gas in the test gas represented by a waveform W1;
    a carrier gas flow system configured to allow a carrier gas to continuously flow into the second space;
    a measurement unit configured to measure a change of concentration of the specimen gas in the carrier gas represented by a waveform W2; and
    an analysis unit that is capable of analyzing a shift in time of the waveform W2 from waveform W1.

6. A method for evaluating dynamic moisture permeability, the method comprising the steps of:
    disposing a sample in a measurement chamber, the sample separating the measurement chamber into a first space and a second space;

allowing a test gas to continuously flow into the first space;

allowing a carrier gas to continuously flow into the second space;

performing control for changing a water vapor concentration in the test gas represented by a waveform W1; and performing analysis based on a shift in time of a waveform W2 indicating change of the water vapor concentration in the carrier gas from the waveform W1.

7. The method for evaluating dynamic moisture permeability according to claim 6, wherein the waveform W1 has periodical change, and waveform analysis is performed in the step of performing analysis based on the waveforms W1 and W2.

8. The method for evaluating dynamic moisture permeability according to claim 7, wherein a frequency of the periodical change of the water vapor concentration in the test gas is changed stepwise or continuously in the step of performing control, and the waveform analysis is performed at each frequency in the step of performing analysis.

9. The method for evaluating dynamic moisture permeability according to claim 6, wherein the water vapor concentration and temperature in the test gas are changed in the step of performing control, and a shift in time of the waveform W2 from the waveform W1 at each temperature is calculated.

10. A method for evaluating dynamic gas permeability, the method comprising the steps of:

disposing a sample in a measurement chamber, the sample separating the measurement chamber into a first space and a second space;

allowing a test gas to continuously flow into the first space;

allowing a carrier gas to continuously flow into the second space;

performing control for changing a concentration of a specimen gas in the test gas represented by a waveform W1; and performing analysis based on a shift in time of a waveform W2 indicating change of the concentration of the specimen gas in the carrier gas from the waveform W1.

11. A non-transitory computer readable recording medium storing a dynamic moisture permeability evaluation program configured to evaluate dynamic moisture permeability of a sample in a measurement chamber separated into a first space and a second space by the sample, the program causing a computer to execute the steps of:

allowing a test gas to continuously flow into the first space;

allowing a carrier gas to continuously flow into the second space;

performing control for changing a water vapor concentration in the test gas represented by a waveform W1; and performing analysis based on a shift in time of a waveform W2 indicating change of the water vapor concentration in the carrier gas from the waveform W1.

12. The non-transitory computer readable recording medium storing the dynamic moisture permeability evaluation program according to claim 11, wherein the waveform W1 has periodical change, and waveform analysis is performed in the step of performing analysis based on the waveforms W1 and W2.

13. The non-transitory computer readable recording medium storing the dynamic moisture permeability evaluation program according to claim 12, wherein a frequency of the periodical change of the water vapor concentration in the test gas is changed stepwise or continuously in the step of performing control, and the waveform analysis is performed it each frequency in the step of performing analysis.

14. The non-transitory computer readable recording medium storing the dynamic moisture permeability evaluation program according to claim 11, wherein the water vapor concentration and temperature in the test gas are changed in the step of performing control, and a shift in time of the waveform W2 from the waveform W1 at each temperature is calculated.

15. A non-transitory computer readable recording medium storing a dynamic gas permeability evaluation program configured to evaluate dynamic gas permeability of a sample in a measurement chamber separated into a first space and a second space by the sample, the program causing a computer to execute the steps of:

allowing a test gas to continuously flow into the first space;

allowing a carrier gas to continuously flow into the second space;

performing control for changing a concentration of a specimen gas in the test gas represented by a waveform W1; and performing analysis based on a shift in time of a waveform W2 indicating change of the concentration of the specimen gas in the earlier gas from the waveform W1.

* * * * *